(12) United States Patent
Pryshchepna et al.

(10) Patent No.: US 10,684,228 B2
(45) Date of Patent: Jun. 16, 2020

(54) SYSTEM AND METHOD OF NEPHELOMETRIC DETERMINATION OF AN ANALYTE

(71) Applicant: Siemens Healthcare Diagnostics Products GmbH, Marburg (DE)

(72) Inventors: Oksana Pryshchepna, Hanau (DE); Wolfgang Steinebach, Salz (DE)

(73) Assignee: Siemens Healthcare Diagnostics Products Products GmbH, Marburg (DE)

( * ) Notice: Subject to any disclaimer, the term of this patent is extended or adjusted under 35 U.S.C. 154(b) by 848 days.

(21) Appl. No.: 14/852,482

(22) Filed: Sep. 11, 2015

(65) Prior Publication Data

US 2016/0084770 A1    Mar. 24, 2016

(30) Foreign Application Priority Data

Sep. 18, 2014    (EP) ..................................... 14185251

(51) Int. Cl.
*G01N 21/51*    (2006.01)
*G01N 15/02*    (2006.01)
(Continued)

(52) U.S. Cl.
CPC ......... *G01N 21/77* (2013.01); *G01N 15/0205* (2013.01); *G01N 21/47* (2013.01); *G01N 21/474* (2013.01); *G01N 21/51* (2013.01); *G01N 33/5304* (2013.01); *G01N 35/00871* (2013.01); *G01N 2015/0693* (2013.01); *G01N 2021/4707* (2013.01); *G01N 2035/00207* (2013.01);
(Continued)

(58) Field of Classification Search
None
See application file for complete search history.

(56) References Cited

U.S. PATENT DOCUMENTS 4,549,809 A    10/1985    Minekane et al.
6,096,561 A    8/2000    Tayi
(Continued)

FOREIGN PATENT DOCUMENTS

CN         1224497 A       7/1999
CN       101983338 A       3/2011
(Continued)

OTHER PUBLICATIONS

Yang Jike et al.: "Introduction to Biomathematics"; 9.6 Second derivative; pp. 208-210; Sep. 30, 1982; 1982.
(Continued)

*Primary Examiner* — Neil N Turk
(74) *Attorney, Agent, or Firm* — Dugan & Dugan, PC

(57) ABSTRACT

A nephelometry system for an automatic analysis device may include a light source, a stop, and a photodetector on the one hand and a receptacle position on the other hand that are movable relative to one another in order to improve the measurement quality of a nephelometry system. The nephelometry system may determine a location of an interval I of recorded light intensity signals which only contains light intensity signals that emerge from a scattered portion of a light beam after passing through a measurement cell placed into the nephelometry system. Methods of nephelometric determination of an analyte are also provided, as are other aspects.

14 Claims, 2 Drawing Sheets

(51) Int. Cl.
    *G01N 21/77*     (2006.01)
    *G01N 21/47*     (2006.01)
    *G01N 33/53*     (2006.01)
    *G01N 35/00*     (2006.01)
    *G01N 15/06*     (2006.01)

(52) U.S. Cl.
    CPC ............... *G01N 2201/068* (2013.01); *G01N 2201/0612* (2013.01)

(56) References Cited

U.S. PATENT DOCUMENTS

| | | |
|---|---|---|
| 6,723,287 B1 | 4/2004 | Ootatsume et al. |
| 6,791,676 B1 | 9/2004 | Meller |
| 7,050,167 B2 | 5/2006 | Meller |
| 2004/0075838 A1* | 4/2004 | Meller ............... G01N 21/474 356/446 |
| 2011/0076199 A1 | 3/2011 | Meller et al. |

FOREIGN PATENT DOCUMENTS

| | | |
|---|---|---|
| EP | 0997726 A2 | 5/2000 |
| EP | 1091205 A2 | 4/2001 |
| EP | 2309251 A1 | 4/2011 |

OTHER PUBLICATIONS

Chinese Search Report of Chinese Application No. 2015105806752 dated Mar. 9, 2018.

* cited by examiner

SYSTEM AND METHOD OF NEPHELOMETRIC DETERMINATION OF AN ANALYTE

CROSS REFERENCE TO RELATED APPLICATION

This claims priority to European Patent Application No. EP 14185251.7, filed Sep. 18, 2014, which is hereby incorporated by reference herein in its entirety for all purposes.

FIELD

The invention relates to a method of nephelometric determination of an analyte and a nephelometry system for an automatic analysis device.

BACKGROUND

These days, a number of detection and analysis methods for determining physiological parameters in body fluid samples or other biological samples are performed in an automated manner and in large numbers in automatic analysis devices, also so-called in vitro diagnostic systems.

Current analysis devices are able to perform a multiplicity of detection reactions and analyses using a sample. In order to be able to perform a multiplicity of examinations in an automated manner, various apparatuses for the spatial transfer of measurement cells, reaction containers, and reagent containers are required, such as, e.g., transfer arms with a gripper function, transport belts or rotatable transport wheels, and apparatuses for transferring liquids, such as, e.g., pipetting apparatuses. The devices comprise a control unit which, by means of appropriate software, is able to plan and work through the work steps for the desired analyses in a largely independent manner.

Many of the analysis methods used in such analysis devices with automated operation are based on optical processes. The determination of clinically relevant parameters, such as, e.g., the concentration or activity of an analyte, is often implemented by virtue of part of a sample being mixed with one or more test reagents in a reaction vessel, which can also be the measurement cell, as a result of which a biochemical reaction or a specific binding reaction is initiated, bringing about a measurable change in an optical or other physical property of the test mix.

In addition to spectrophotometry, nephelometry is a widely used analysis process. By way of example, nephelometry renders it possible to determine the concentration of finely distributed, colloidal particles in liquids or gases quantitatively. If a suspension of small particles is introduced into a light beam, part of the entering light is absorbed. Another part, which is also referred to as a primary beam, leaves the suspension without being scattered, and a further part is scattered laterally in relation to the entering beam. In nephelometry, this laterally emerging scattered light is measured.

Nephelometry is predominantly used for the quantitative or qualitative detection of analytes, such as, e.g., proteins, which are detectable by means of a specific binding reaction between specific binding partners, e.g., by means of an antigen/antibody binding.

A nephelometry system comprises at least one light source, at least one photodetector and at least one receptacle position for a measurement cell. Typically, the arrangement of light source and light detector is selected in such a way that the scattered light is measurable, wherein scattered light is scattered by macromolecules to be detected in the sample, e.g., by particle aggregates which are produced as a result of an analyte-dependent reaction in a reaction mix.

Different set-ups are commercially available, which differ in terms of the arrangement of light source, receptacle position for the measurement cell, and photodetector. By way of example, in one set-up, the photodetector can be arranged laterally from the light beam emitted by the light source in order to register the scattered light in an angle range of 90° in relation to the direction of the light beam emitted by the light source. This is advantageous in that the intensity of the scattered light can be relatively low and the influence of the measurement by the non-scattered part of the light beam emitted by the light source, which is referred to as primary beam, is relatively small.

In another set-up, light source, receptacle position, and photodetector can be arranged in such a way that the photodetector registers the scattered light in the angle ranges around the propagation direction of the light beam emitted by the light source in which the intensity of the scattered light is relatively high. However, not only the scattered light but also the primary beam reaches the photodetector in this geometry. However, since only the scattered part of the light is intended to contribute to the measurement result, complete blocking of the primary beam is required for an optimization of the measurement result.

Optical stops are usually used to block the primary beam. These are held in the beam path by means of thin attachments, such as, e.g., wires, and adapted in terms of the size and shape thereof in such a way that they preferably completely block the primary beam such that, where possible, only scattered light is incident on the detector. Preferably, the ratio of scattered light portions to primary beam portions is less than 0.001.

Analysis devices in which either the optical unit is movable relative to the measurement cells or in which the measurement cells are movable relative to the optical unit are becoming more widespread. This is advantageous in that a multiplicity of samples can be examined virtually simultaneously by using one optical unit, significantly increasing the sample throughput.

EP-A1-2309251 has described an apparatus for the photometric examination of samples, in which the measurement cells have a stationary embodiment and are arranged in a circular arc-shaped manner, while the optical unit moves along the measurement cell arrangement in a circular arc-shaped manner.

In such optical systems, in which the optical unit is moved relative to the measurement cell (or vice versa), the light beam travels along a route, preferably across the measurement cell, and a plurality of measurement values are registered, wherein each individual measurement value originates from a different position in the measurement cell due to the movement. As a result, a typical, well-shaped curve (see FIG. 1) with a first, falling flank, a curve base, and a second, rising flank is generated in nephelometric measurements. When the measurement cell enters into (falling flank) and exits from (rising flank) the primary beam, the light of the primary beam is incident on the measurement cell walls, reflected or refracted and guided past the stop, which is in fact intended to block the primary beam, to the photodetector. The significant region for determining the analyte lies in the region of the curve base, where the blocking of the primary beam is at a maximum. Furthermore, there is a change in respect of the location of the scattering volume in the measurement cell between subsequent measurements in time of the same sample as a result of mechanical tolerances of the moving portion, which is important if, for example, reaction kinetics are intended to be registered.

SUMMARY

Therefore, for a precise analyte determination, it is necessary to select those light intensity signals from the totality of the measured light intensity signals for further evaluation that emerge from the scattered portion of the light beam after passing through the measurement cell and that, where possible, do not have a primary light portion.

Thus, it is an object of the invention to improve the measurement quality of a nephelometry system, in which the light source, the stop, and the photodetector on the one hand and the receptacle position on the other hand are movable relative to one another.

The object is achieved by virtue of the location of an interval I which only contains light intensity signals that emerge from the scattered portion of the light beam after passing through the measurement cell and that have no, or only an insignificant, primary light portion being determined automatically from the totality of the light intensity signals that are recorded during the travel of the light beam along a route through the measurement cell.

According to one aspect, a method of nephelometric determination of an analyte in a sample, with the sample being situated in a measurement cell, is provided. The method includes the following:

(a) placing the measurement cell into a nephelometry system comprising at least one optical unit, the optical unit comprising at least one light source for emitting a light beam, a stop for blocking the non-scattered portion of the light beam after passing through the measurement cell, and a photodetector for receiving scattered portions of the light beam after passing through the measurement cell;

(b) moving the measurement cell and/or moving the optical unit such that the light beam emitted by the light source passes through the measurement cell along a route;

(c) recording the light intensity signals received by the photodetector along the route, along which the light beam emitted by the light source travels through the measurement cell;

(d) determining the location of an interval I of the recorded light intensity signals which only contains light intensity signals that emerge from the scattered portion of the light beam after passing through the measurement cell, wherein the size of the interval I emerges from a defined number of light intensity signals and is a predetermined parameter for the employed nephelometry system; and (e) determining the analyte on the basis of a light intensity signal or on the basis of a mean value for a plurality of light intensity signals from the interval I of the recorded light intensity signals.

The location of the interval I of the recorded light intensity signals is established by virtue of the light intensity signals recorded along the route being evaluated as follows:

forming the first and second derivative of the light intensity signals recorded along the route;

determining a first position Ff along the route with the conditions $f'(x)<0$ and $f''(x)=0$;

determining a second position Fs along the route with the conditions $f'(x)>0$ and $f''(x)=0$;

determining a third position M along the route by applying the formula $M=Ff+(Fs-Ff)/2$; and positioning the interval I such that the position M forms the center of the interval I.

BRIEF DESCRIPTION OF THE DRAWINGS

The embodiments depicted in the figures in an exemplary manner are intended to elucidate the present invention and should not be construed as being restrictive. In detail.

DETAILED DESCRIPTION

Figure 1:
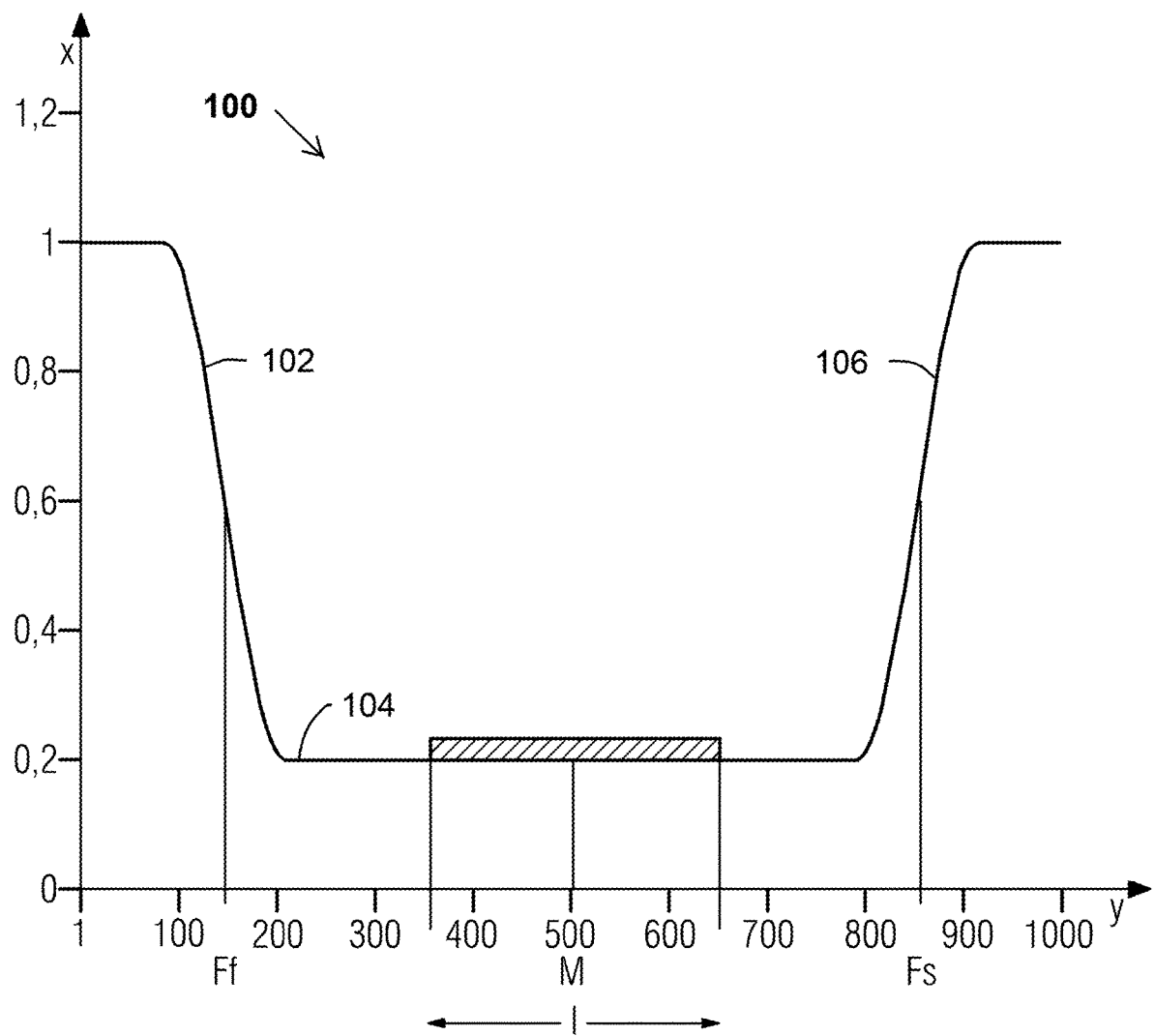
FIG. 1 shows a typical well-shaped profile of a light intensity signal curve, which was recorded in a nephelometry system in which a plurality of receptacle positions for respectively one measurement cell with a circular diameter are arranged stationary on a circular arc and in which the optical unit, i.e., light source, stop, and photodetector, moves in a circular path along the receptacle positions.

The size of the interval I (see FIG. 1) emerges from a defined number of light intensity signals and is a predetermined parameter for the employed nephelometry system. The parameter depends on the size, the geometry and the material of the measurement cell, on the speed with which the primary beam is moved across the measurement cell, on the size, geometry and arrangement of the stop for blocking the non-scattered portion of the light beam, on the number of the light intensity signals which are recorded during a pass, etc. Therefore, for a given nephelometry system, the number of successive light intensity signals which are typically obtained when measuring a typical sample in a typical measurement cell, which light intensity signals only emerge from the scattered portion of the light beam after passing through the sample/measurement cell, i.e., in which the blocking of the primary beam is at a maximum, is to be established empirically. When setting the specific size of the interval I for the employed nephelometry system, a number of light intensity signals which is as large as possible is firstly to be sought after, because this brings about a large signal-to-noise ratio; secondly, the size of the interval I should be selected to be so small that it is ensured that neither the start value nor the end value of the interval I ever comes to rest in the region of the falling or rising flank of the signal curve, as shown in FIG. 1.

By way of example, in an exemplary nephelometry system with an optical unit rotating about measurement cells which are arranged in a circular arc-shaped and stationary manner (rotational speed 2 Hz) and with plastic measurement cells with a circular cross section and a diameter of approximately 7 mm and the light intensity signals which are recorded during a pass of the light beam through a measurement cell numbering approximately 1000, an interval I with a size of 300 light intensity signals was established and set for the nephelometry system in preliminary trials.

The first position Ff, determined as described above, corresponds to the point of inflection of the falling flank of the well-shaped signal curve.

The second position Fs, determined as described above, corresponds to the point of inflection of the rising flank of the well-shaped signal curve.

In one embodiment of the method, the method steps (b)-(d) above are repeated at least n times and determining the analyte in step (e) is implemented on the basis of the mean value of respectively one light intensity signal from the n+1 intervals I or on the basis of a mean value from n+1 mean values of a plurality of light intensity signals from the n+1 intervals I of the recorded light intensity signals. By way of example, n is a number from 1 to 50, preferably a number from 10 to 20. Multiple measurement of the same sample increases the precision of the quantitative determination of the analyte.

In another embodiment of the method, the method steps (b)-(d) are repeated at least n times and determining the analyte in step (e) is implemented on the basis of the change in respectively one light intensity signal from the n+1 intervals I over time or on the basis of the change of a mean value of a plurality of light intensity signals from the n+1 intervals I of the recorded light intensity signals over time. By way of example, n is a number from 1 to 1000. This renders it possible to record reaction kinetics, the parameters of which, such as, e.g., maximum gradient, area under the curve, etc., can be used for the quantitative determination of the analyte.

A "sample" should be understood to mean a composition which probably contains the analyte to be determined. Conventional samples in in vitro diagnostics consist of or contain at least blood, plasma, serum, urine, saliva, liquor, ear secretions, nasal secretions, or other bodily fluids, or body tissue samples or cells held in a liquid. In particular, the term "sample" also comprises reaction mixes, i.e., mixtures of the actual sample with one or more reagents, e.g., antibody-coated latex particles, in which the amount or activity of the analyte can be determined on the basis of change in an optical property.

Figure 2:
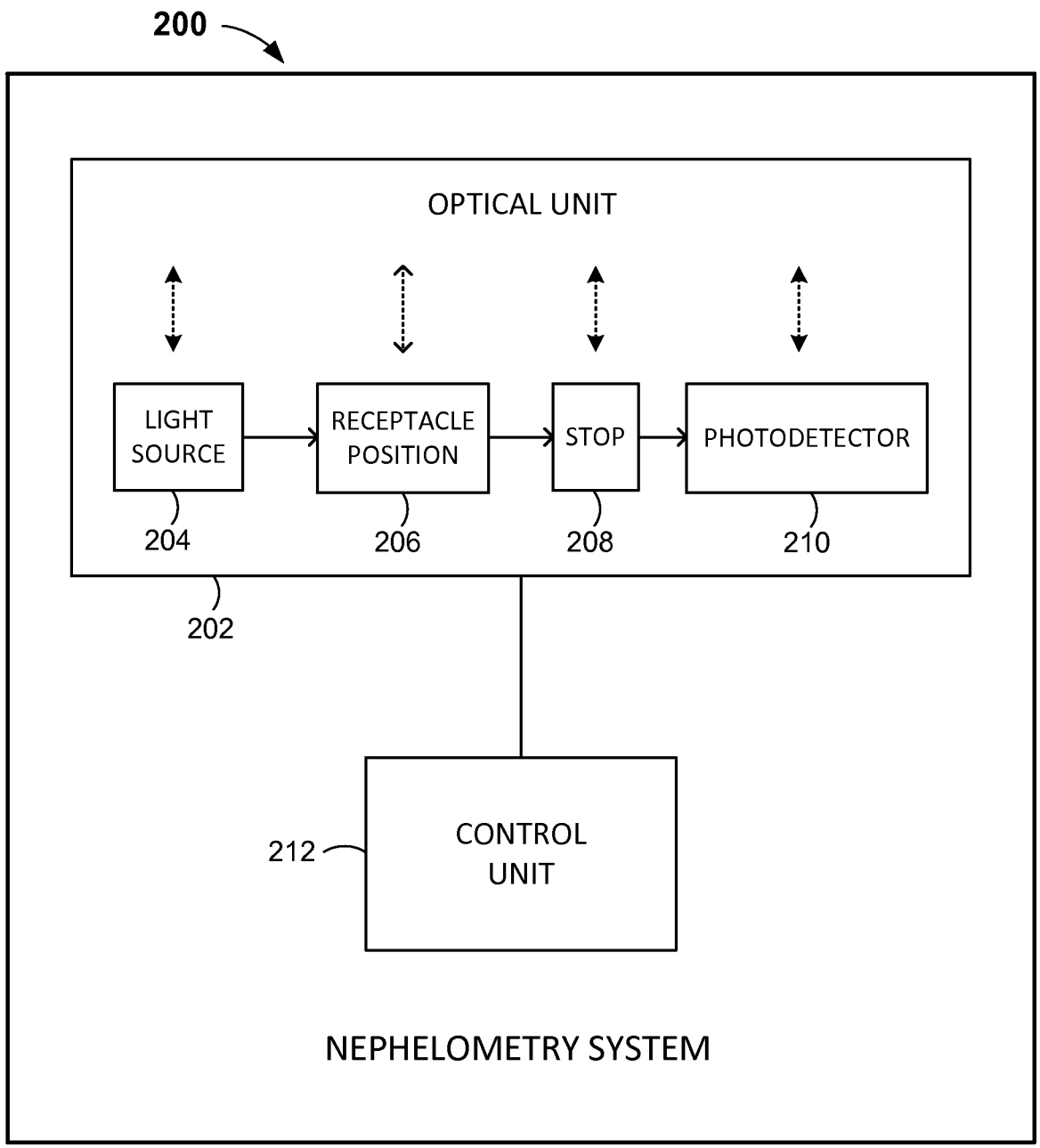
FIG. 2 illustrates a block diagram of a nephelometry system according to embodiments.

Further subject matter of the present invention includes a nephelometry system 200 as shown in FIG. 2. The nephelometry system 200 comprises at least one optical unit 202, which has at least one light source 204 for emitting a light beam, at least one receptacle position 206 for a measurement cell, a stop 208 for blocking the non-scattered portion of the light beam after passing through a measurement cell arranged in the receptacle position 206, and a photodetector 210 for receiving scattered portions of the light beam after passing through the measurement cell. The light source 204, the stop 208, and the photodetector 210 on the one hand and the receptacle position 206 on the other hand are movable relative to one another. Furthermore, the nephelometry system 200 according to the invention has a control unit 212 which controls a method comprising the following:

moving the measurement cell and/or moving the optical unit such that the light beam emitted by the light source passes through the measurement cell along a route;

recording the light intensity signals received by the photodetector along the route, along which the light beam emitted by the light source travels through the measurement cell;

determining the location of an interval I of the recorded light intensity signals which only contains light intensity signals that emerge from the scattered portion of the light beam after passing through the measurement cell, wherein the size of the interval I emerges from a defined number of light intensity signals and is a predetermined parameter for the employed nephelometry system; and determining an analyte on the basis of a light intensity signal or on the basis of a mean value for a plurality of light intensity signals from the interval I of the recorded light intensity signals, wherein the location of the interval I of the recorded light intensity signals is established by virtue of the light intensity signals recorded along the route being evaluated as follows:

forming the first and second derivative of the light intensity signals recorded along the route;

determining a first position Ff along the route with the conditions f'(x)<0 and f''(x)=0;

determining a second position Fs along the route with the conditions f'(x)>0 and f''(x)=0;

determining a third position M along the route by applying the formula M=Ff+(Fs−Ff)/2; and positioning the interval I such that the position M forms the center of the interval I.

A preferred light source has a laser diode. However, provision can likewise be made for the light source to be a light emitting diode (LED), an incandescent lamp, a gas-discharge lamp or an arc clamp. Advantageously, the light source emits light in wavelength ranges between 200 nm and 1400 nm, preferably between 300 and 1100 nm.

The light detector is preferably a photodiode, which converts visible light, and in some embodiments also IR light or UV light, into an electric current or voltage by the inner photoelectric effect. This process is also referred to as signal recording and the electric current or voltage is also referred to as a light intensity signal. Alternatively, the light detector is a CCD (charge-coupled device) sensor. CCD sensors consist of a matrix or a line with light-sensitive photodiodes. However, provision can likewise be made for the light detector to be a photocell, a silicon photodetector, an avalanche photodetector, or a photomultiplier.

The stop for blocking the primary beam, i.e., the non-scattered portion of the light beam after passing through the measurement cell, is arranged in such a way that the primary beam is absorbed and/or reflected.

In principle, the optical unit of the nephelometry system according to the invention can furthermore also have filters, lenses, mirrors, or other optical elements.

Preferably, a nephelometry system according to the invention has at least two, preferably at least 16, particularly preferably at least 32 receptacle positions for respectively one measurement cell.

Furthermore preferably, the at least two receptacle positions for respectively one measurement cell are arranged along a circular path and the light source, the stop, and the photodetector are movable along a circular path relative to the receptacle positions for respectively one measurement cell, or the receptacle positions for the measurement cells are movable along a circular path relative to the light source, stop, and photodetector.

Preferably, the at least one receptacle position is suitable for receiving a measurement cell with an oval or round cross section.

A further subject matter of the present invention is an automatic analysis device which contains a nephelometry system according to the invention.

A preferred automatic analysis device furthermore comprises a container for receiving a multiplicity of measurement cells as bulk material, an apparatus for separating the measurement cells, and an apparatus for positioning a single measurement cell in the at least one receptacle position of the optical unit of the nephelometry system. With the aid of such an analysis device, it is possible to perform fully automatic nephelometric analyte determinations in a multiplicity of samples.

Referring to FIG. 1, a curve 100 shows the measured light intensity (X-axis) as a function of the route (Y-axis) along which the light beam travels through a measurement cell. The curve 100 is composed of 1000 measurement points or light intensity signals, which were recorded during the one-time travel along the route of the light beam through one of the measurement cells with a sample. In the system described herein in an exemplary manner, the distance between two measurement points is 1.33 μm or 1.06 μs. In reality, the curves obtained thus appear less ideal as a result of interference, noise, and asymmetry in the mechanics; however, the obtained raw data can be subject to conventional filtering for smoothing the curve. It is possible to identify that the curve 100 has a first, falling flank 102, a curve base 104, and a second, rising flank 106. The region that is significant for determining the analyte lies in the region of the curve base 104, where the blocking of the primary beam is at a maximum. Using the method according to the invention, the point of inflection Ff of the falling flank 102 and the point of inflection Fs of the rising flank 106 are determined. Then, the point M is sought-after, which lies precisely in the middle between the points Ff and Fs, and the interval I predetermined for the nephelometry system used here (300 light intensity signals/measurement points large in this case), which interval only contains light intensity signals that emerge from the scattered portion of the light beam after passing through the measurement cell, is positioned in such a way that the point M forms the center of the interval I. Evaluating the light intensity signals obtained in the interval I enables a precise determination of the analyte.

What is claimed is:

1. A method of nephelometric determination of an analyte in a sample, with the sample being situated in a measurement cell, the method comprising:
   (a) placing the measurement cell into a nephelometry system comprising at least one optical unit, the optical unit comprising at least one light source for emitting a light beam, a stop for blocking the non-scattered portion of the light beam after passing through the measurement cell and a photodetector for receiving scattered portions of the light beam after passing through the measurement cell;
   (b) moving the measurement cell or moving the optical unit such that the light beam emitted by the light source passes through the measurement cell along a route;
   (c) recording the light intensity signals received by the photodetector along the route while moving, along which the light beam emitted by the light source travels through the measurement cell and plotting the light intensity signals received in a signal-time curve;
   (d) determining the location of an interval I of the recorded light intensity signals within a region of the plotted signal-time curve, wherein the interval I only contains light intensity signals that emerge from the scattered portion of the light beam after passing through the measurement cell, wherein the size of the interval I emerges from a defined number of light intensity signals and is a predetermined parameter for the employed nephelometry system; and
   (e) determining the analyte on the basis of a light intensity signal or on the basis of a mean value for a plurality of light intensity signals from the interval I of the recorded light intensity signals;
   wherein the location of the interval I of the recorded light intensity signals within the plotted signal-time curve is established by the light intensity signals recorded along the route evaluated as follows:
      forming the first and second derivative of the light intensity signals recorded along the route;
      determining a first position Ff in the plotted signal-time curve with the conditions $f'(x)<0$ and $f''(x)=0$;
      determining a second position Fs in the plotted signal-time curve with the conditions $f'(x)>0$ and $f''(x)=0$;
      determining a third position M in the plotted signal-time curve by applying the formula $M=Ff+(Fs-Ff)/2$; and
      positioning the interval I in the plotted signal-time curve such that the position M forms the center of the interval I.

2. The method as claimed in claim 1, wherein the method steps (b)-(d) are repeated n times and wherein determining the analyte in step (e) is implemented on the basis of the mean value of respectively one light intensity signal from the n+1 intervals I or on the basis of a mean value from n+1 mean values of the plurality of light intensity signals from the n+1 intervals I of the recorded light intensity signals.

3. The method as claimed in claim 1, wherein the method steps (b)-(d) are repeated n times and wherein determining the analyte in step (e) is implemented on the basis of the change in respectively one light intensity signal from the n+1 intervals I or on the basis of the change of a mean value of a plurality of light intensity signals from the n+1 intervals I of the recorded light intensity signals over time.

4. A nephelometry system comprising at least one optical unit, the optical unit comprising at least one light source for emitting a light beam, at least one receptacle position for a measurement cell, a stop for blocking the non-scattered portion of the light beam after passing through a measurement cell arranged in the receptacle position, and a photodetector for receiving scattered portions of the light beam after passing through the measurement cell, wherein the light source, the stop, and the photodetector on the one hand and the receptacle position on the other hand are movable relative to one another, wherein the nephelometry system further comprises a control unit configured to cause the following:
   move the measurement cell or the optical unit such that the light beam emitted by the light source passes through the measurement cell along a route;
   record the light intensity signals received by the photodetector along the route while moving, along which the light beam emitted by the light source travels through the measurement cell and plot the light intensity signals received in a signal-time curve;
   determine the location of an interval I of the recorded light intensity signals within a region of the plotted signal-time curve, wherein the interval I only contains light intensity signals that emerge from the scattered portion of the light beam after passing through the measurement cell, wherein the size of the interval I emerges from a defined number of light intensity signals and is a predetermined parameter for the nephelometry system; and
   determine an analyte on the basis of a light intensity signal or on the basis of a mean value for a plurality of light intensity signals from the interval I of the recorded light intensity signals,
   wherein the location of the interval I of the recorded light intensity signals within the plotted signal-time curve is established by virtue of the light intensity signals recorded along the route evaluated as follows:
      forming the first and second derivative of the light intensity signals recorded along the route;
      determining a first position Ff in the plotted signal-time curve with the conditions $f'(x)<0$ and $f''(x)=0$;
      determining a second position Fs in the plotted signal-time curve with the conditions $f'(x)>0$ and $f''(x)=0$; and determining a third position M in the plotted signal-time curve by applying the formula M=Ff+(Fs−Ff)/2; and positioning the interval I in the plotted signal-time curve such that the position M forms the center of the interval I.

5. The nephelometry system as claimed in claim 4 comprising at least two receptacle positions for one measurement cell.

6. The nephelometry system as claimed in claim 5, wherein at least two of the receptacle positions are arranged along a circular path.

7. The nephelometry system as claimed in claim 4, wherein the light source, the stop, and the photodetector are movable along a circular path relative to the at least one receptacle position.

8. The nephelometry system as claimed in claim 7, wherein the at least one receptacle position is movable relative to the light source, the stop, and the photodetector.

9. An automatic analysis device, comprising a nephelometry system as claimed in claim 8, and further comprising a container for receiving a multiplicity of measurement cells as bulk material, an apparatus for separating the measurement cells, and an apparatus for positioning a single measurement cell in the at least one receptacle position of the nephelometry system.

10. The nephelometry system as claimed in claim 4, wherein the at least one receptacle position is movable relative to the light source, the stop, and the photodetector.

11. The nephelometry system as claimed in claim 4, wherein the at least one receptacle position is configured to receive a measurement cell with an oval or round cross section.

12. An automatic analysis device, comprising a nephelometry system as claimed in claim 4, and further comprising a container for receiving a multiplicity of measurement cells as bulk material, an apparatus for separating the measurement cells, and an apparatus for positioning a single measurement cell in the at least one receptacle position of the nephelometry system.

13. The nephelometry system as claimed in claim 4 comprising at least 16 receptacle positions for one measurement cell.

14. The nephelometry system as claimed in claim 4 comprising at least 32 receptacle positions for one measurement cell.

* * * * *